US00PP30145P2

(12) United States Plant Patent
Bradford et al.

(10) Patent No.: US PP30,145 P2
(45) Date of Patent: Jan. 29, 2019

(54) NECTARINE TREE NAMED 'PEARLICIOUS XX'

(50) Latin Name: *Prunus persica*
Varietal Denomination: Pearlicious XX

(71) Applicants: Lowell Glen Bradford, Le Grand, CA (US); Jon M. Quisenberry, Le Grand, CA (US)

(72) Inventors: Lowell Glen Bradford, Le Grand, CA (US); Jon M. Quisenberry, Le Grand, CA (US)

( * ) Notice: Subject to any disclaimer, the term of this patent is extended or adjusted under 35 U.S.C. 154(b) by 0 days.

(21) Appl. No.: 15/732,740

(22) Filed: Dec. 26, 2017

(51) Int. Cl.
*A01H 5/08* (2018.01)

(52) U.S. Cl.
USPC ..... Plt./188

(58) Field of Classification Search
USPC ..... Plt./188
See application file for complete search history.

(56) References Cited

U.S. PATENT DOCUMENTS

PP24,835 P3 9/2014 Bradford

*Primary Examiner* — Annette H Para

(57) ABSTRACT

The present invention relates to a new and distinct variety of nectarine tree, *Prunus persica*, broadly characterized by a medium size, moderately vigorous, hardy, self-fertile, productive and regular bearing tree. The variety blooms during the late season and requires about 650 chilling hours. The fruit matures under the ecological conditions described in late September, with first picking on Sep. 25, 2017. The fruit is uniform, medium in size, sub-acidic and sweet in flavor, globose in shape, clingstone in type, firm in texture, white in flesh color, fairly red in skin color, and has a bitter tasting kernel.

1 Drawing Sheet

Botanical classification: *Prunus persica.*
Variety denomination: 'PEARLICIOUS XX'.

BACKGROUND OF THE VARIETY

In a continuing effort to improve the quality of shipping fruits, we, the inventors, typically hybridize a large number of peach, nectarine, plum, apricot, and cherry seedlings each year. We also grow a smaller number of open pollinated seeds of each of these fruits, usually to capture recessive traits. The present invention relates to a new and distinct variety of nectarine tree, which has been denominated varietally as 'Pearlicious XX'.

In 2003 we made a first generation hybridization using '52P564' (unpatented) nectarine as the selected seed parent and '37P398' (unpatented) nectarine as the selected pollen parent. Upon reaching maturity the fruit of this hybridization was gathered, and the seeds were removed, cracked, stratified, germinated, and grown as seedlings on their own root in our greenhouse facility. Upon reaching dormancy we transplanted them to a cultivated area of our experimental orchard located near Le Grand, Calif., in Merced County (San Joaquin Valley). During the fruit evaluation season of 2008 we selected the present variety as a single tree from the group of seedlings described above. Subsequent to origination of the present variety of nectarine tree, we asexually reproduced it by budding and grafting in the experimental orchard described above, and such reproduction of plant and fruit characteristics were true to the original tree in all respects. The reproduction of the variety included the use of 'Nemaguard' (unpatented) rootstock upon which the present variety was compatible and true to type.

The present variety is similar to its seed parent, '52P564' (unpatented) nectarine, by being self-fertile and by producing nectarines that are mostly red in skin color, that are clingstone in type, that are medium to large in size, and that ripen in the late season, but is quite distinguished from it by producing fruit that is white instead of yellow in flesh color, that is sub-acidic instead of acidic in flavor, that is much sweeter, and that ripens about two weeks later.

The present variety is similar to its pollen parent, '37P398' (unpatented) nectarine, by being self-fertile and by producing nectarines that are mostly red in skin color, white in flesh color, clingstone in type, and sub-acidic in flavor, but is quite distinguished from it by producing fruit that is larger in size, that has less skin freckling, and that ripens about two weeks later.

The present variety is most similar to 'Pearlicious XVII' (U.S. Plant Pat. No. 24,835) nectarine by having a moderate size tree, by having showy blossoms, by being self-fertile, by requiring about 650 chilling hours, and by producing nectarines that are fairly red in skin color, white in flesh color, clingstone in type, firm in texture, fairly globose in shape, and very sweet in flavor, but is distinguished therefrom by producing nectarines that are somewhat smaller in size, that have a bitter instead of sweet kernel, and that mature about twenty-five days later.

SUMMARY OF VARIETY

In summary, the present nectarine variety is characterized by a medium size, moderately vigorous, hardy, self-fertile, productive and regular bearing tree. The variety blooms during the late season and requires about 650 chilling hours. The fruit matures under the ecological conditions described in late September, with first picking on Sep. 25, 2017. The fruit is uniform, medium in size, sub-acidic and sweet in flavor, globose in shape, clingstone in type, firm in texture, white in flesh color, fairly red in skin color, and has a bitter tasting kernel.

DRAWING

The accompanying photograph consists of four whole fruits positioned to display the characteristics of the skin color and form, one sliced fruit to reveal the flesh and stone, typical leaves, and four insets depicting the flower buds and blossoms as they appear on the tree during the blooming season.

POMOLOGICAL CHARACTERISTICS

Referring now more specifically to the pomological characteristics of this new and distinct variety of nectarine tree, the following has been observed under the ecological conditions prevailing near Le Grand, Merced County (San Joaquin Valley), Calif., and was developed at the state of firm ripe on Oct. 3, 2017, on a multiplied tree using 'Nemaguard' (unpatented) rootstock during its sixth growing season. The blossom and flower descriptions were made the previous blooming season. All major color code designations are by reference to the Inter-Society Color Council, National Bureau of Standards. Common color names are also used occasionally.

PARENTAGE

Seed parent: '52P564' (unpatented) nectarine.
Pollen parent: '37P398' ((unpatented) nectarine.

TREE

Size: Medium, reaching and maintaining a height of 8' [2.44 m.] and a spread of 7' [2.13 m.] after six growing seasons utilizing typical dormant pruning.
Vigor: Medium vigor, responding about average to irrigation and fertilization. The variety grows about 2' [0.61 m.] of surplus top-growth during the spring and summer. The plant should be grown on a standard commercial rootstock for production purposes.
Growth: Upright and dense.
Form: Pruned to a vase shape.
Hardiness: Hardy with respect to central California winters.
Heat tolerance: Observed to perform adequately in typical central California climatic conditions, which typically include extended periods of heat.
Drought tolerance: Variety is developed for commercial orchards and requires regular irrigation.
Production: Productive, thinning usually necessary.
Fertility: Self-fertile.
Bearing: Regular bearer, with no crop failures observed.
Chilling requirement: About 650 hours.
Leaf bud burst: Medium to late, during the end of flowering.
Trunk:
- *Size.*—Stocky, reaching a maximum diameter of 4" [101.6 mm.] after the sixth growing season.
- *Texture.*—Medium to shaggy.
- *Bark color.*—A Light grayish yellowish brown [79. l.gy.yBr] and Grayish yellowish brown [80. gy.yBr] variegation with Brownish orange [54. brO] crevices present.
- *Lenticels.*—Approximate Number Per Square Inch: 8. Color: Strong yellowish brown [74. s.yBr]. Average Size: ⅛" [3.2 mm.] in length. The width is typically one fourth as much as the length. Shape: Eye-shaped.

Branches:
- *Size.*—Medium to slender, diameter of main scaffold is 1¾" [44.5 mm.] measured 12" above the crotch, diameter of limb is 1¼" [31.8 mm.] measured 12" above the first fork.
- *Texture.*—Smooth on first and second year wood, increasing in roughness with age.
- *Color.*—1st Year Wood Topside: Grayish red [19. gy.R]. 1st Year Wood Underside: Brilliant yellow green [116. brill.YG]. 3rd Year Wood: A Grayish yellowish brown [80. gy.yBr] and Moderate yellowish brown [77. m.yBr] variegation with Strong yellowish brown [74. s.yBr] crevices present.
- *Lenticels.*—Number Per Square Inch: About 25 on second year wood. Color: Brownish orange [54. brO]. Average Size: Medium, 1/16" [1.6 mm.] in length. The width is typically one fourth as much as the length. Shape: Eye-shaped.

Leaves:
- *Size.*—Medium. Average Length: 5¾" [146 mm.]. Average Width: 1½" [38.1 mm.].
- *Arrangement.*—Alternate.
- *Thickness.*—Medium.
- *Form.*—Elliptical.
- *Apex.*—Acuminate.
- *Base.*—Acute to rounded.
- *Surface.*—Smooth on both sides.
- *Color.*—Dorsal Surface: Moderate olive green [125. m.OlG]. Ventral Surface: Moderate yellow green [120. m.YG].
- *Red midvein.*—Present.
- *Margin.*—Finely serrate.
- *Venation.*—Pinnately net veined.
- *Petiole.*—Average Length: ⅜" [9.5 mm.]. Average Thickness: 1/16" [1.6 mm.]. Color: Light yellow green [119. l.YG].
- *Stipules.*—Number: 2 per leaf, up to 6 per growing tip. Average Length: ¼" [6.4 mm.]. Color: Vivid yellow green [115. v.YG] becoming Moderate brown [58. m.Br] with age.
- *Glands.*—Number: 2 to 6 per leaf. Position: Alternate, first pair is located at the intersection of petiole and base of blade. Form: Reniform. Size: Medium, about 1/32" [0.8 mm.] in length, about 1/64" [0.4 mm.] in width. Color: Brilliant yellow green [116. brill.YG].
- *Leaf buds.*—Pointed.

Flower buds:
- *Hardiness.*—Hardy, with respect to central California blooming season.
- *Diameter.*—Typically ⅜" [9.5 mm.] 1 week before bloom.
- *Length.*—Typically ⅝" [15.9 mm.] 1 week before bloom.
- *Form.*—Not appressed.
- *Surface.*—Slightly pubescent.
- *Tip color.*—Moderate purplish pink [250. m.pPk].

Flowers: Perfect, complete, perigynous, usually a single pistil, about thirty stamens, five sepal and petal locations alternately positioned.
- *Type.*—Showy, large.
- *Average flower diameter.*—1¾" [44.5 mm.].
- *Average flower depth.*—7/16" [11.1 mm.] when fully open.

*Average pedicel length.*—7/64" [2.8 mm.].
*Number of petals.*—Mostly five, extra petal fragments common, double blossoms occasionally observed.
*Petal arrangement.*—Overlapping.
*Petal shape.*—Circular to oval.
*Petal margin.*—Entire, quite wavy.
*Average petal diameter.*—5/8" [15.9 mm.].
*Average petal length.*—11/16" [17.5 mm.].
*Petal apex.*—Rounded.
*Petal base.*—Rounded to somewhat truncate.
*Petal color.*—Light pink [4. l.Pk] toward the apex, Moderate pink [5. m.Pk] toward the base on both sides.
*Anther color.*—Dark reddish orange [38. d.rO] at bloom onset.
*Pollen.*—Anthers produce an abundance of Brilliant yellow [83. brill.Y] pollen.
*Stigma color.*—Light yellow green [119. l.YG].
*Stigma position.*—Typically located about even with the nearby anthers.
*Stamen position.*—Typically located about 1/32" [0.8 mm.] below the petals.
*Ovary.*—Non-pubescent.
*Sepal color.*—Dark purplish red [259. d.pR] on the outer surface. The inner surface is a somewhat translucent Pinkish white [9. pkWhite] with both Grayish purplish red [262. gy.pR] and Vivid yellow green [115. v.YG] areas visible.
*Sepal length.*—5/16" [7.9 mm.].
*Sepal width.*—1/4" [6.4 mm.].
*Sepal apex.*—Rounded to elliptical to match the sepal length and width.
*Sepal margin.*—Fairly smooth.
*Average pistil length.*—9/16" [14.3 mm.].
*Average stamen length.*—1/2" [12.7 mm.].
*Fragrance.*—Moderate.
*Blooming period.*—Late compared to other varieties, five days after 'Pearlicious XVII' (U.S. Plant Pat. No. 24,835) nectarine.
*Onset of bloom.*—One percent on Feb. 27, 2017.
*Date of full bloom.*—Mar. 9, 2017.
*Duration of bloom.*—One to two weeks, dependent on ambient temperature.
*Bloom density.*—Heavy.
*Number per cluster.*—1 to 3 with single flowers most common.

FRUIT

Maturity when described: Firm ripe, Oct. 3, 2017.
Date of first picking: Sep. 25, 2017.
Date of last picking: Oct. 8, 2017.
Size: Uniform, medium.
*Average diameter axially.*—2 7/8" [73.0 mm.].
*Average diameter across suture plane.*—2 3/4" [69.9 mm.].
*Average diameter across cheek plane.*—2 3/4" [69.9 mm.].
*Typical weight.*—7.09 ounces [201 grams].
Form: Uniform, globose to round ovate, mostly symmetrical.
*Longitudinal section form.*—Round to oval.
*Axial view.*—Round.
Suture: A shallow trough extending from the base, along the side, and ending with a slight depression just beyond pistil point.
*Near the base.*—A shallow groove.
*Along the side.*—A shallow trough.
*Near the apex.*—A shallow groove.
Ventral surface: Rounded, lipped throughout on both sides.
Lips: Slightly unequal.
Cavity: Flaring, circular, suture showing on one side, Pale greenish yellow [104. p.gY] stem markings present.
*Depth.*—7/16" [11.1 mm.].
*Breadth.*—1 1/8" [28.6 mm.].
Base: Truncate, slightly cordate if viewed parallel to the suture.
Apex: Rounded.
Pistil point: Apical, short, about 1/16" [1.6 mm.] in length.
Stem: Medium.
*Average length.*—3/8" [9.5 mm.].
*Average width.*—3/16" [4.8 mm.].
Skin:
*Thickness.*—Medium.
*Surface.*—Smooth.
*Tenacity.*—Tenacious to the flesh.
*Astringency.*—Nonastringent.
*Tendency to crack.*—None observed.
*Color.*—Strong red [12. s.R] over a Pale greenish yellow [104. p.gY] background with some Dark red [16. d.R] mottling throughout.
Flesh:
*Color.*—Yellowish white [92. yWhite] with some Moderate red [15. m.R] streaking next to the stone.
*Surface of pit cavity.*—Covered with Moderate red [15. m.R] broken fibers when twisted away from the stone.
*Amygdalin.*—Scarce.
*Juice.*—Moderate, rich.
*Texture.*—Genetically melting, but remains firm and crisp throughout the harvest period.
*Fibers.*—Few, fine, tender.
*Ripens.*—Fairly even.
*Flavor.*—Sub-acidic, sweet, typically 18 to 20 brix.
*Aroma.*—Slight.
*Eating quality.*—Very good.

STONE

Type: Clingstone.
Form: Elliptical.
Hilum: Narrow, oblong.
Base: Rounded, slightly oblique.
Apex: Acute.
Sides: Equal.
Tip: Acute, not sharp.
Surface: Irregularly furrowed toward the apex, pitted toward the base.
Ridges: Jagged.
External color: Deep reddish brown [41. deep rBr] when first removed.
Pit wall color when cracked: Strong brown [55. s.Br].
Cavity surface color: Strong yellowish brown [74. s.yBr].
Average pit wall thickness: 1/4" [6.4 mm.].
Average length: 1 3/8" [34.9 mm.].
Average width: 1" [25.4 mm.].
Average breadth: 3/4" [19.1 mm.].
Tendency to split: None observed.

Kernel:

*Form.*—Oval.

*Skin color.*—Strong yellowish brown [74. s.yBr].

*Pellicle color.*—Dark brown [59. d.Br].

*Vein color.*—Moderate brown [58. m.Br].

*Taste.*—Bitter.

*Viable.*—Yes.

*Average length.*—¾" [19.1 mm.].

*Average width.*—7/16" [11.1 mm.].

*Amygdalin.*—Abundant.

USE

Market: Fresh market and long distance shipping.

Keeping quality: Good, fruit quality observed to remain in good condition after 17 days in standard cold room at 36° Fahrenheit [2° Celsius].

Shipping quality: Good.

Resistance to insects: Not tested.

Resistance to diseases: Not tested.

OTHER NOTES

Although the new variety of nectarine tree possesses the described characteristics under the ecological conditions at Le Grand, Calif., in the central part of the San Joaquin Valley, it is to be expected that variations in these characteristics may occur when farmed in areas with different climatic conditions, different soil types, and/or varying cultural practices.

We claim:

1. A new and distinct variety of nectarine tree, substantially as illustrated and described, that is most similar to 'Pearlicious XVII' (U.S. Plant Pat. No. 24,835) nectarine by having a moderate size tree, by having showy blossoms, by being self-fertile, by requiring about 650 chilling hours, and by producing nectarines that are fairly red in skin color, white in flesh color, clingstone in type, firm in texture, fairly globose in shape, and very sweet in flavor, but is distinguished therefrom by producing nectarines that are somewhat smaller in size, that have a bitter instead of sweet kernel, and that mature about twenty-five days later.

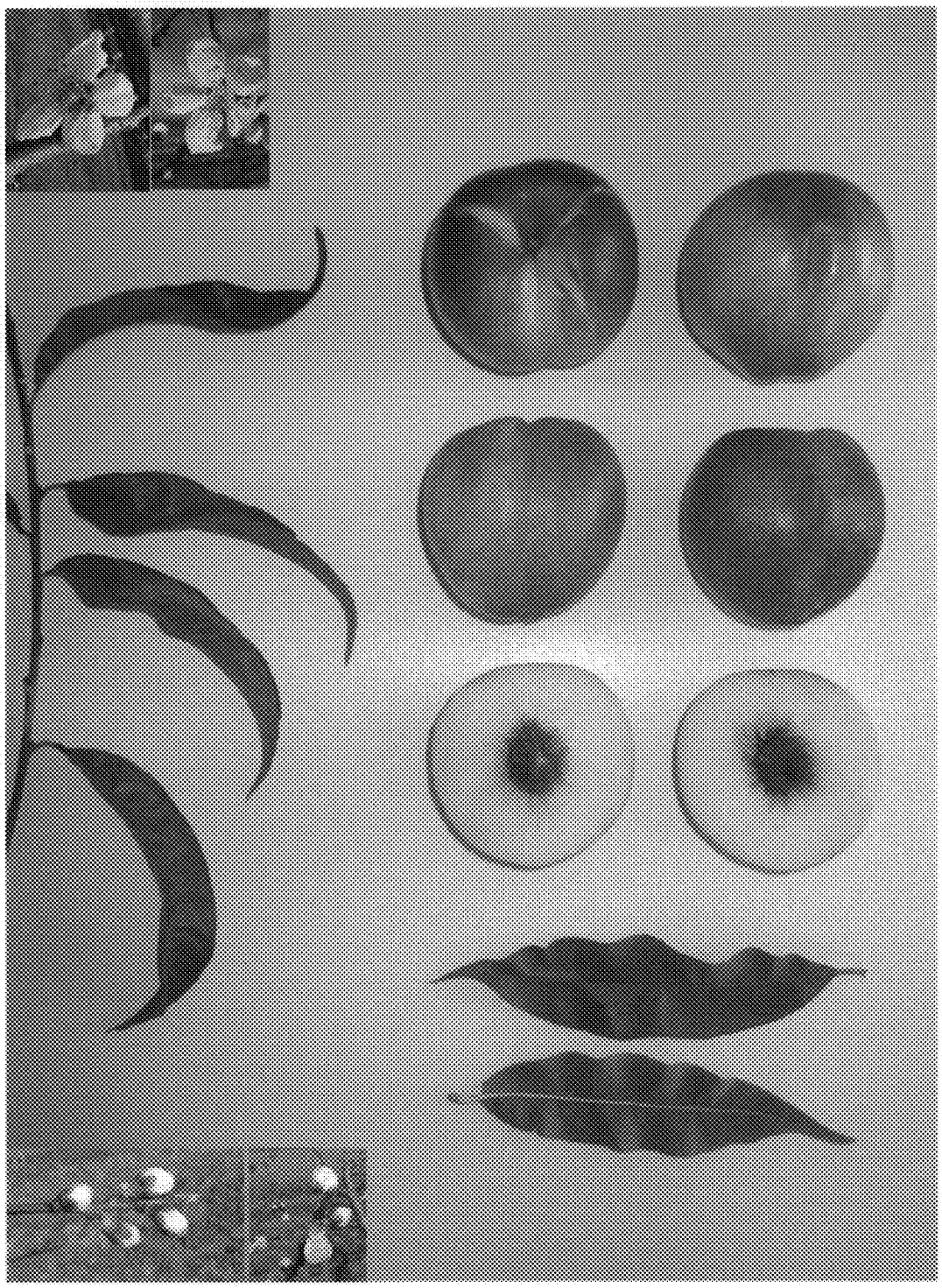

* * * * *